United States Patent
Luybansky (10) Patent No.: US 10,959,898 B2
(45) Date of Patent: Mar. 30, 2021

(54) PATIENT TABLE AND PATIENT WEIGHT MEASURING SYSTEM

(71) Applicant: General Electric Company, Schenectady, NY (US)

(72) Inventor: Michael Luybansky, Haifa (IL)

(73) Assignee: GENERAL ELECTRIC COMPANY, Schenectady, NY (US)

(*) Notice: Subject to any disclaimer, the term of this patent is extended or adjusted under 35 U.S.C. 154(b) by 338 days.

(21) Appl. No.: 16/196,345

(22) Filed: Nov. 20, 2018

(65) Prior Publication Data

US 2020/0155402 A1 May 21, 2020

(51) Int. Cl.
*A61B 6/04* (2006.01)
*A61G 13/06* (2006.01)
*A61G 13/00* (2006.01)
*A61G 13/12* (2006.01)

(52) U.S. Cl.
CPC ............ *A61G 13/06* (2013.01); *A61B 6/0442* (2013.01); *A61G 13/0018* (2013.01); *A61G 13/126* (2013.01); *A61G 2203/32* (2013.01); *A61G 2203/44* (2013.01)

(58) Field of Classification Search
CPC ...... A61G 13/06; A61G 13/0018; A61B 6/04; A61B 6/0442
See application file for complete search history.

(56) References Cited

U.S. PATENT DOCUMENTS

| | | | |
|---|---|---|---|
| 2006/0277683 A1* | 12/2006 | Lamire | A61G 7/015 5/600 |
| 2009/0252300 A1* | 10/2009 | Schwartz | A61B 5/0555 378/209 |
| 2010/0031443 A1 | 2/2010 | Georgiev et al. | |
| 2013/0081204 A1 | 4/2013 | Ramos et al. | |
| 2015/0216747 A1* | 8/2015 | Valentino | A61G 1/0237 5/610 |
| 2015/0320382 A1 | 11/2015 | Martinez Ferreira et al. | |
| 2016/0374630 A1 | 12/2016 | Smith et al. | |
| 2017/0020466 A1 | 1/2017 | Moulin et al. | |

* cited by examiner

*Primary Examiner* — Fredrick C Conley
(74) *Attorney, Agent, or Firm* — The Small Patent Law Group LLC; Dean D. Small (57) ABSTRACT

Patient weight measuring system includes a patient table and a control circuit. The patient table includes a tabletop that receives a patient thereon, an elevation mechanism, and a load sensor. The elevation mechanism adjusts a height of the tabletop relative to a floor. The elevation mechanism includes a support frame and an actuator. The support frame includes multiple pivotable frame members mechanically connected to the tabletop. The actuator is configured to exert an actuator force on at least one of the frame members to control the height of the tabletop. The load sensor is operably connected to the actuator and configured to measure the actuator force. The control circuit is communicatively connected to the load sensor, and is configured to calculate a weight of the patient disposed on the tabletop based on the actuator force measured by the load sensor.

21 Claims, 5 Drawing Sheets

| $L_{cr}$ (cm) | h (cm) | $F_{act}$ (N) | $W_p$ (kg) | $W_p$ (lb) |
|---|---|---|---|---|
| 0 | 48 | 813 | 100 | 220 |
| 100 | 48 | 813 | 100 | 220 |
| 0 | 48 | 859 | 125 | 276 |
| 0 | 48 | 768 | 75 | 165 |
| 0 | 70 | 460 | 100 | 220 |
| 0 | 32 | 1327 | 100 | 220 |

PATIENT TABLE AND PATIENT WEIGHT MEASURING SYSTEM

FIELD

The subject matter disclosed herein relates generally to weighing patients in a medical environment.

BACKGROUND

Measuring and recording a patient's weight is a standard practice in medical facilities, such as clinics, hospitals, doctor's offices, physical therapy centers, and the like. The patient weight is typically acquired during a discrete weight-measuring task in which the patient is asked to stand on a scale and a medical worker records the measured weight in a file. The weight-measuring task may be performed prior to the patient being admitted to an examination room to consult with a doctor or other medical professional and/or to perform medical imaging, surgery, or another medical task. The discrete weight-measuring task is generally inefficient because it delays the impending examination of the patient and the examination of other patients scheduled to be examined after the patient. Furthermore, the weight-measuring task may be difficult and/or embarrassing for some patients. For example, disabled patients may have difficulty standing on a scale, and overweight patients may experience anxiety as the medical worker views and records the readout of the scale.

BRIEF DESCRIPTION

In one or more embodiments, a patient table is provided that includes a tabletop, an elevation mechanism, a load sensor, and a control circuit. The tabletop is configured to receive a patient thereon. The elevation mechanism is configured to adjust a height of the tabletop relative to a floor. The elevation mechanism includes a support frame and an actuator. The support frame includes multiple pivotable frame members mechanically connected to the tabletop. The actuator is configured to exert an actuator force on at least one of the frame members to control the height of the tabletop. The load sensor is operably connected to the actuator and configured to measure the actuator force. The control circuit is communicatively connected to the load sensor, and is configured to calculate a weight of the patient disposed on the tabletop based on the actuator force measured by the load sensor.

In one or more embodiments, a patient weight measuring system is provided that includes a patient table and a control circuit. The patient table includes a tabletop, a support frame, an actuator, and a load sensor. The tabletop is configured to receive a patient thereon. The support frame includes multiple pivotable frame members mechanically connected to the tabletop. Two of the frame members intersect one another at a point of intersection and are pivotably connected to one another via a link at the point of intersection to define a scissor linkage. The actuator is configured to modify an actuator force exerted by the actuator on at least one of the two frame members of the scissor linkage to adjust a height of the tabletop relative to a floor. The load sensor engages the actuator and is configured to measure the actuator force. The control circuit is communicatively connected to the load sensor of the patient table. The control circuit is configured to calculate a weight of the patient disposed on the tabletop based on the actuator force measured by the load sensor.

In one or more embodiments, a patient table is provided that includes a tabletop, an elevation mechanism, a load sensor, and a control circuit. The tabletop includes a platform and a cradle that is slidably coupled to the platform. The cradle is controllable to move relative to the platform between a retracted position and an extended position. The cradle receives a patient thereon, and a first end of the cradle projects beyond a first end of the platform in the extended position to load the patient into a gantry of an imaging system. The elevation mechanism is configured to adjust a height of the tabletop relative to a floor. The elevation mechanism includes a support frame and an actuator. The support frame includes multiple pivotable frame members mechanically connected to the tabletop. The actuator is configured to exert an actuator force on at least one of the frame members in a direction along an actuator load axis to control the height of the tabletop. The load sensor is operably connected to the actuator and configured to measure the actuator force along the actuator load axis. The control circuit is communicatively connected to the load sensor. The control circuit is configured to calculate a weight of the patient disposed on the cradle based on the actuator force measured by the load sensor while the cradle is at either of the retracted position or the extended position.

In one or more embodiments, a method (e.g., for measuring patient weight) is provided. The method includes obtaining an actuator force measured by a load sensor on a patient table. The patient table includes a tabletop configured to receive a patient thereon, and also includes an elevation mechanism that has a support frame and an actuator. The support frame has multiple pivotable frame members mechanically connected to the tabletop. The actuator is configured to exert the actuator force on at least one of the frame members to control a height of the tabletop relative to a floor. The load sensor is disposed along an actuator load axis of the actuator, and the actuator force is measured by the load sensor while the patient is on the tabletop. The method also includes determining, via one or more processors, a weight of the patient that is disposed on the patient table based on the actuator force measured by the load sensor.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

One or more embodiments of the inventive subject matter described herein provide a patient weight measuring system that is configured to automatically weigh a patient as the patient sits or lies on a patient table. For example, instead of asking the patient to stand on a scale, a medical facility that includes the patient weight measuring system described herein can skip the separate weight-measuring task and bring the patient directly to a medical room that includes the patient table. The patient table may be utilized for medical imaging, such that a region of the patient's body is imaged while the patient is disposed on the patient table. For example, the patient table may be used with various medical imaging modalities, such as a Positron Emission Tomography (PET) imaging system, a Single Photon Emission Computed Tomography (SPECT) imaging system, a Computed Tomography (CT) imaging system, a Magnetic Resonance Imaging (MRI) imaging system, an X-Ray imaging system, an ultrasound imaging system, and/or the like. The patient weight measuring system disclosed herein is configured to automatically measure the weight of the patient before, during, and/or after a medical imaging procedure while the patient is disposed on the patient table. The patient weight measuring system is not limited to medical imaging applications, and the patient table thereof can be located in offices and rooms in which consultations, check-ups, physicals, and the like, are performed.

According to at least one embodiment, the patient table of the patient weight measuring system includes a tabletop, an elevation mechanism, a load sensor, and a control circuit. The elevation mechanism is configured to adjust a height of the tabletop relative to a floor or other stationary reference point. The patient sits and/or lies on the tabletop. The elevation mechanism includes a support frame and an actuator. The actuator may be motor-controlled to move pivotable frame members of the support frame to adjust the height of the tabletop. The load sensor is configured to measure an actuator force exerted by the actuator on the support frame. The control circuit receives the actuator force that is measured by the load sensor and calculates a weight of the patient on the tabletop based on the actuator force.

At least one technical effect of the subject matter described herein includes increased efficiency and patient throughput at a medical facility by omitting the separate weight-measuring task prior to admitting a patient to an examination room. At least another technical effect includes providing a reduced cost and complexity than weight measuring furniture that measures a person's weight based on multiple different sensors distributed along the furniture. At least another technical effect may include an increased accuracy in the measured weight of a patient relative to other weight measuring furniture that measures a person's weight based on multiple different sensors distributed along the furniture because errors or inconsistencies may aggregate across the multiple different sensors to generate a less accurate weight measurement than the patient weight measuring system described herein. Yet another technical effect of the patient weight measuring system described herein is the ability to measure the weight of a patient regardless of the location of the patient's center of mass along a length of the table, even if the patient is disposed on a cantilevered cradle that projects outward beyond the rest of the table. For example, the patient weight measuring system accommodate changes in leverage attributable to different positions of the patient on the table to accurately measure the weight of the patient, even if the patient is moved by the cradle to a cantilevered position.

Figure 1:
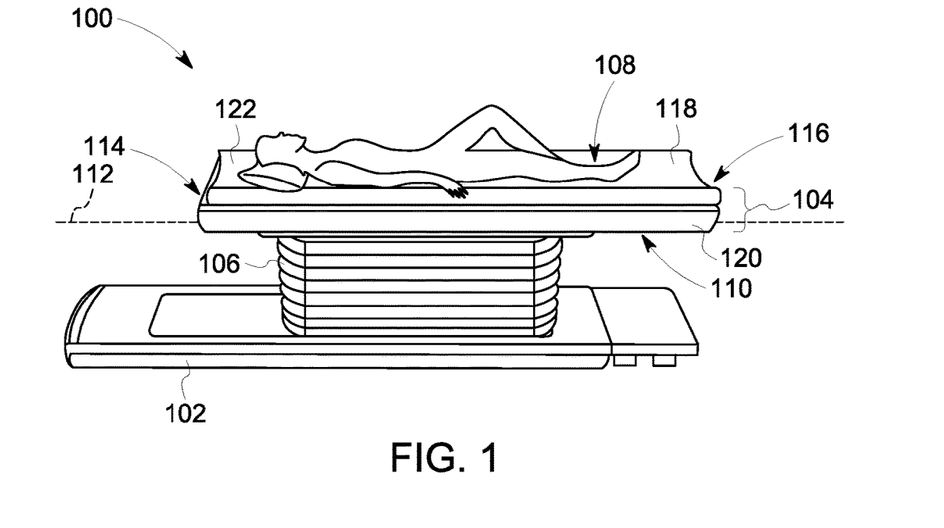
FIG. 1 illustrates a patient table according to an embodiment.

FIG. 1 illustrates a patient table 100 according to an embodiment. The patient table 100 represents at least a portion of a patient weight measuring system 200 shown in FIG. 2 configured to automatically weigh a patient that is disposed on the patient table 100 (also referred to herein as table 100). The table 100 includes a base 102, a tabletop 104, and a pedestal or column 106 between the base 102 and the tabletop 104. The pedestal 106 is mechanically connected to the tabletop 104 and the base 102. The base 102 is disposed on a floor. The pedestal 106 and the base 102 support and hold the tabletop 104 in a lifted position above the floor.

The tabletop 104 has a top side 108 and a bottom side 110 that is opposite the top side 108. As used herein, relative or spatial terms such as "top," "bottom," "front," "rear," "upper," and "lower" are only used to identify and distinguish the referenced elements according to the illustrated orientations and do not necessarily require particular positions or orientations relative to the surrounding environment of the patient table 100 or the patient weight measuring system 200 (shown in FIG. 2). The pedestal 106 engages the bottom side 110. The patient sits or lies on the top side 108. The tabletop 104 is elongated along a longitudinal axis 112 from a first end 114 to a second end 116 that is opposite the first end 114. The tabletop 104 may have a length configured to permit the patient to lie on the tabletop in a reclined or recumbent position without hanging over the ends 114, 116. For example, the length may be greater than the height of a majority of patients, such as greater than the height of an adult man in the 95% percentile of height.

In at least one embodiment, the tabletop 104 includes a cradle 118 and a platform 120. The platform 120 is rigidly connected to the pedestal 106, and may define the bottom side 110 of the tabletop 104. The cradle 118 may define at least a portion of the top side 108 of the tabletop 104. The patient sits or lies on the cradle 118. The cradle 118 is slidably connected to the platform 120, and is extendable relative to the platform 120. For example, the cradle 118 may be moveable relative to the platform 120 (and the base 102 and pedestal 106) between a retracted position and an extended position. The cradle 118 is in the retracted position in FIG. 1. At least a portion of the cradle 118 projects beyond an edge of the platform 120 in the extended position. As used herein, the term extended position may refer to a range of multiple different positions of the cradle 118 in which a portion of the cradle 118 projects or overhangs beyond the platform 120 in a cantilevered arrangement. The cradle 118 may be extendable to load the patient thereon into a gantry of an imaging system or device, such as an MRI imaging system, a CT imaging system, or the like. The cradle 118 has a top surface 122 that may be contoured or flat. The table 100 may include a cushion, pad, or mattress on the top surface 122 of the cradle 118 to provide comfort and support for the patient.

Figure 2:
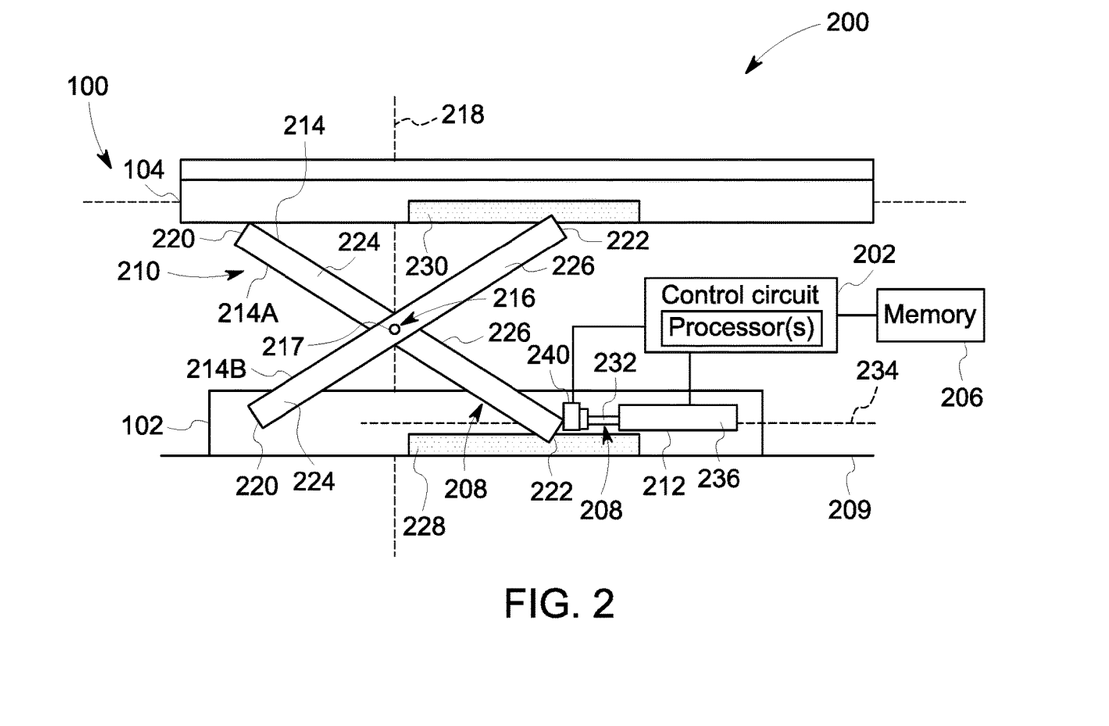
FIG. 2 illustrates a patient weight measuring system that includes the patient table according to an embodiment.

FIG. 2 illustrates the patient weight measuring system 200 according to an embodiment. The patient weight measuring system 200 includes the patient table 100 and a control circuit 202. The control circuit 202 includes one or more processors 204 and associated circuitry. For example, the control circuit 202 includes and/or represents one or more hardware circuits or circuitry that include, are connected with, or that both include and are connected with the one or more processors 204, controllers, and/or other hardware logic-based devices. The control circuit 202 may include a central processing unit (CPU), one or more microprocessors, a graphics processing unit (GPU), or any other electronic component capable of processing inputted data according to specific logical instructions.

The control circuit 202 may be operably connected to a memory storage device 206 (referred to herein as memory 206). The memory 206 is a tangible and non-transitory computer readable medium. The memory 206 may include or represent a flash memory, RAM, ROM, EEPROM, and/or the like. The control circuit 202 may execute programmed instructions stored on the memory 206 or stored on another tangible and non-transitory computer readable medium. For example, the control circuit 202 may be configured to calculate a weight of a patient that is disposed on the table 100 by executing the programmed instructions stored on the memory 206. The memory 206 optionally may store additional information that is accessible to and utilized by the control circuit 202 as described herein, such as look-up tables, mathematical equations, calibration constants, body mass index (BMI) charts, and/or the like.

In an embodiment, the control circuit 202 and the memory 206 are integrated components of the patient table 100. For example, the control circuit 202 and memory 206 may be parts of a computing device mechanically housed in or on the patient table 100. The computing device may have a user interface and display that are accessible to a medical technician at the patient table 100. Alternatively, the control circuit 202 and the memory 206 may be discrete and separate from the patient table 100. For example, the control circuit 202 and the memory 206 may be components of a remote device, such as a handheld tablet, smartphone, or workstation of a medical technician, nurse, or doctor. The remote device may communicate with one or more components of the patient table 100 via wired cables and/or wireless signals.

The patient table 100 shown in FIG. 2 is a simplified version of the patient table 100 shown in FIG. 1. FIG. 2 shows additional components of the patient table 100 that are not visible in FIG. 1. For example, the patient table 100 includes an elevation mechanism 208 that is configured to adjust and control a height of the tabletop 104 relative to the floor 209. The elevation mechanism 208 is configured to move the tabletop 104 along a vertical or height axis 218 to adjust the height of the tabletop 104. The elevation mechanism 208 may be disposed at least partially within the pedestal 106 (shown in FIG. 1) and the base 102. The elevation mechanism 208 includes a support frame 210 and an actuator 212. The support frame 210 includes multiple frame members 214 mechanically connected to the tabletop 104. The frame members 214 are linear and elongate arms or beams in the illustrated embodiment. The frame members 214 are pivotable relative to each other and/or relative to the base 102 and tabletop 104.

Figure 8:
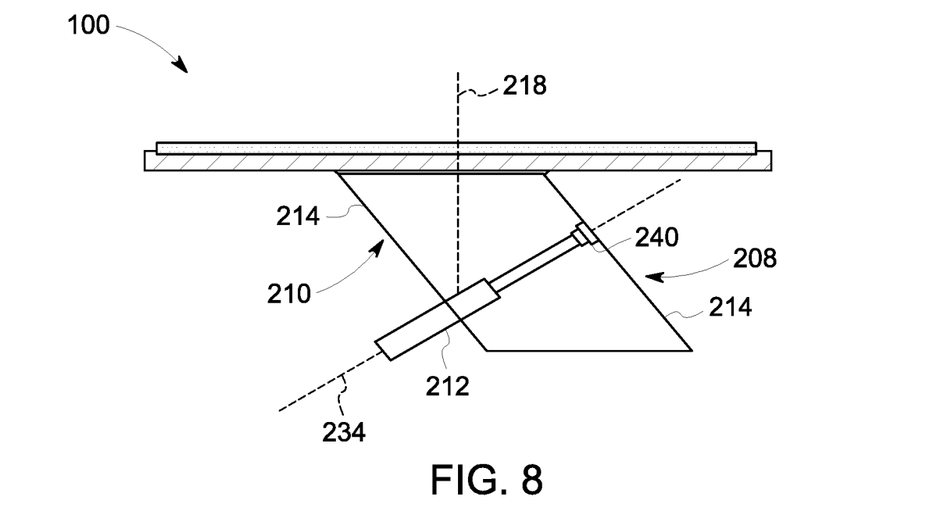
FIG. 8 illustrates the patient table with the elevation mechanism modified according to a second alternative embodiment.

In the illustrated embodiment, the support frame 210 includes or defines a scissors linkage. For example, the two frame members 214 shown in FIG. 2 intersect one another at a point of intersection 216 and are pivotably connected to one another via a link 217 at the point of intersection 216. The two frame members 214 are able to pivot relative to one another about an axis of the link 217. The link 217 may be an axle, shaft, post, or the like. The point of intersection 216 is spaced apart from respective first and second ends 220, 222 of each of the two frame members 214. For example, each frame member 214 includes a first segment 224 between the point of intersection 216 and the first end 220 of the frame member 214, and a second segment 226 between the point of intersection 216 and the second end 222 of the frame member 214. The scissors linkage resembles an "X" shape in FIG. 2. In an alternative embodiment, the support frame 210 may lack a scissors linkage such that the pivotable frame members 214 do not cross one another to resemble an "X" shape. For example, the support frame 210 may have a parallelogram shape, as shown in FIG. 8.

In FIG. 2, the first end 220 of one frame member 214A is pivotably coupled to the tabletop 104, and the second end 222 of the frame member 214A is slidably coupled to the base 102. For example, the base 102 includes a linear rail or track 228. The second end 222 of the frame member 214A is secured to the linear rail 228 and moves (e.g., slides) along the linear rail 228 based on an actuator force exerted by the actuator 212 on the support frame 210. The first end 220 of the other frame member 214B shown in FIG. 2 is pivotably coupled to the base 102, and the second end 222 of the frame member 214B is slidable coupled to the tabletop 104. The tabletop 104 includes a linear rail or track 230 to which the second end 222 of the frame member 214B is secured. The second end 222 of the frame member 214B moves (e.g., slides) along the linear rail 230 based on the actuator force exerted by the actuator 212. Optionally, the first ends 220 of the two frame members 214A, 214A are pivotably secured in fixed locations to the tabletop 104 and base 102, respectively, such that the first ends 220 do not translate relative to the tabletop 104 and base 102, unlike the second ends 222.

Although FIG. 2 shows two frame members 214A, 214B, the support frame 210 may include more than two frame members 214. For example, at least one additional pair of crisscrossing frame members 214 may be disposed behind the visible pair of frame members 214A, 214B. Alternatively, the support frame 210 may include multiple pairs of crisscrossing frame members 214 connected end to end to span the height between the base 102 and the tabletop 104 instead of the illustrated embodiment in which each of the frame members 214A, 214B extends the full height between the base 102 and the tabletop 104. In an alternative embodiment, the frame members 214 may have a parallelogram arrangement instead of the scissors linkage shown in FIG. 2.

The actuator 212 exerts an actuator force on at least one of the frame members 214 to control the height of the tabletop 104 relative to the floor 209. For example, the actuator 212 can increase the actuator force to raise the tabletop 104 along the vertical axis 218, and can decrease the actuator force to lower the tabletop 104 along the vertical axis 218. The actuator 212 may be any of various types of actuation devices able to perform the operations of the actuator described herein. The actuator 212 in the illustrated embodiment is a linear actuator that includes a linear bolt or rod 232 that moves along an actuator load axis 234 and exerts the actuator force in a direction parallel to the actuator load axis 234. The actuator 212 controls an extension distance of the bolt 232 from a housing 236 of the actuator 212 that is secured in a fixed position to the table 100. The bolt 232 of the actuator 212 may be powered by electric current, hydraulic fluid pressure, pneumatic pressure, or the like. In a non-limiting example, the actuator 212 may include an induction motor that rotates a gear (e.g., bevel gear, worm gear, or the like), and the rotation of the gear is mechanically transmitted to the bolt 232 via threads along the bolt 232 to control the extension distance of the bolt 232 relative to the stationary housing 236. In the illustrated embodiment, the actuator 212 is mounted to and/or within the base 102. The bolt 232 exerts the actuator force on the second end 222 of the frame member 214A in FIG. 2, but may engage the other frame member 214B in addition to or instead of the frame member 214A in an alternative embodiment.

In an alternative embodiment, the actuator 212 may be disposed on or within the tabletop 104 instead of the base 102. For example, the actuator 212 may exert the actuator force on the second end 222 of the frame member 214B to control the height of the tabletop 104.

The patient measuring system 200 also includes a load sensor 240 that is mounted on the patient table 100. The load sensor 240 is operably connected to the actuator 212 and is configured to measure the actuator force exerted by the actuator 212 on the support frame 210. It is recognized that the force exerted by the actuator 212 on the support frame 210 is equivalent to the opposite force exerted by the support frame 210 on the actuator 212, and the actuator force refers to either of the two equal and opposite forces. The load sensor 240 may have a resistance than varies with applied force, such that the load sensor 240 converts force, pressure, weight, and/or the like into a change in electrical resistance. The load sensor 240 may be or include a strain gauge, a load cell, a piezoelectric element, or the like. In the illustrated embodiment, the load sensor 240 is disposed between the bolt 232 of the actuator 212 and the second end 222 of the frame member 214A. The load sensor 240 measures the actuator force exerted by the actuator 212 on the frame member 214A. The load sensor 240 is located in-line with the actuator load axis 234. Optionally, the load sensor 240 may have a different position along the actuator load axis 234 than the position in FIG. 2, such as between the bolt 232 and the housing 236 of the actuator 212 or between the housing 236 and the base 102. The load sensor 240 may be discrete from the actuator 212 and may be usable with any of various different types of actuation devices that represent the actuator 212.

The load sensor 240 is communicatively connected to the control circuit 202 via a wired or wireless communication link. For example, the load sensor 240 may be connected via a wire or cable to the control circuit 202 or the load sensor 240 may transmit or broadcast a wireless signal to the control circuit 202. The load sensor 240 is configured to communicate electrical signals representative of force measurements to the control circuit 202. For example, the load sensor 240 communicates signals representing measurements of the actuator force to the control circuit 202, either periodically or upon request by the control circuit 202.

The control circuit 202 is configured to calculate the weight of a patient sitting or lying on the tabletop 104 based on an actuator force measurement received from the load sensor 240. According to one or more embodiments described herein, the actuator force measured by the load sensor 240 may be the only force measurement utilized by the control circuit 202 to calculate the weight of the patient disposed on the tabletop 104. For example, the control circuit 202 calculates the weight of the patient based on the actuator force measurement of the single load sensor 240 independent of any other force sensors that may be disposed on the table 100 or proximate to the table 100. The use of a single load sensor 240 may reduce cost and/or complexity relative to conceivable weight-measuring furniture that measures the force at each of multiple furniture support locations, such as at each of four legs of a table or chair.

Optionally, the control circuit 202 may be operably connected to the actuator 212. For example, the control circuit 202 may receive actuator position signals from the actuator 212 that indicate a position of actuator 212. The position of the actuator 212 may refer to a current extension length of the bolt 232 from the housing 236 or the like. The control circuit 202 may be configured to determine the height of the tabletop 104 relative to the floor 209 (or to the base 102) based on the actuator position signal. In at least one embodiment, the control circuit 202 may factor the height of the tabletop 104 in the calculation to determine the weight of the patient. For example, the height of the tabletop 104 may affect the weight calculation, as described in more detail herein. Optionally, the control circuit 202 may be configured to control the movement of the actuator 212, such that the control circuit 202 may communicate control signals to the actuator 212. Alternatively, the control circuit 202 receives the actuator position signals from the actuator 212 but does not control the actuator 212 because the actuator 212 is controlled by a separate control device.

Figure 3:
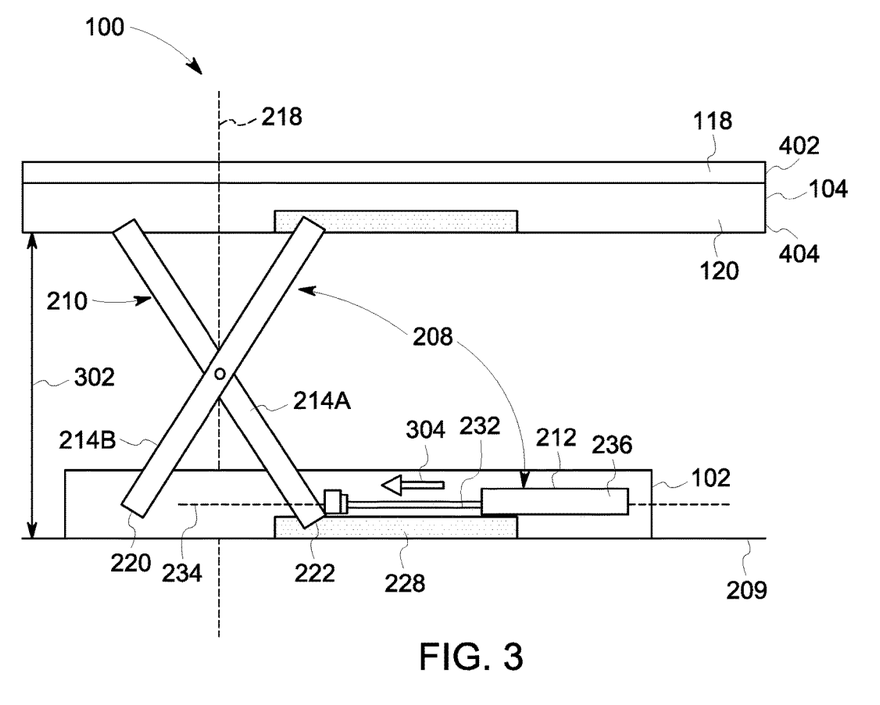
FIG. 3 illustrates the patient table of the patient weight measuring system at a raised position relative to the position of the patient table shown in FIG. 2.

FIG. 3 illustrates the patient table 100 of the patient weight measuring system 200 (shown in FIG. 2) at a raised position relative to the position of the patient table 100 shown in FIG. 2. For example, the tabletop 104 has a greater height 302 from the floor 209 in the raised position relative to the position (e.g., lowered position) shown in FIG. 2. The elevation mechanism 208 is configured to adjust the height of the tabletop 104 by moving the tabletop 104 parallel to the vertical axis 218. For example, the tabletop is raised upward (e.g., away from the base 102) by the actuator 212 exerting the actuator force on the second end 222 of the frame member 214A of the support frame 210 to cause the second end 222 to move towards the first end 220 of the other frame member 214B. The second end 222 slides along the linear rail 228 of the base 102. Due to the scissor linkage, the movement of the frame member 214A causes both frame members 214A, 214B to pivot in opposite rotational directions, which pushes the tabletop 104 upward away from the base 102. The actuator 212 exerts the actuator force in a direction 304 that is parallel to the actuator load axis 234. In the illustrated embodiment, the actuator load axis 234 is perpendicular to the vertical axis 218. Therefore, the actuator 212 exerts the actuator force on the frame member 214A in the direction 304 that is perpendicular to the vertical axis 218, which causes movement of the tabletop 104 along the vertical axis 218.

The actuator 212 raises the height of the tabletop 104 by increasing the extension length of the bolt 232 relative to the housing 236 of the actuator 212. As shown in FIG. 3, the length of the bolt 232 extending from the housing 236 of the actuator 212 is greater than the extension length of the bolt 232 in the lowered position shown in FIG. 2. The actuator force is the force required to overcome the resistive forces and allow the bolt 232 to extend outward from the housing 236 to a designated position. The actuator 212 can lower the height of the tabletop 104 by retracting the bolt 232 to reduce the extension length of the bolt 232, which reduces the actuator force exerted on the frame member 214A. Optionally, biasing forces due to gravity and/or the like may cause the tabletop 104 to automatically lower as the bolt 232 is retracted. Alternatively, the bolt 232 may be mechanically secured to the frame member 214A such that retraction of the bolt 232 pulls the second end 222 of the frame member 214A along the linear rail 228 towards the housing 236.

Figure 4:
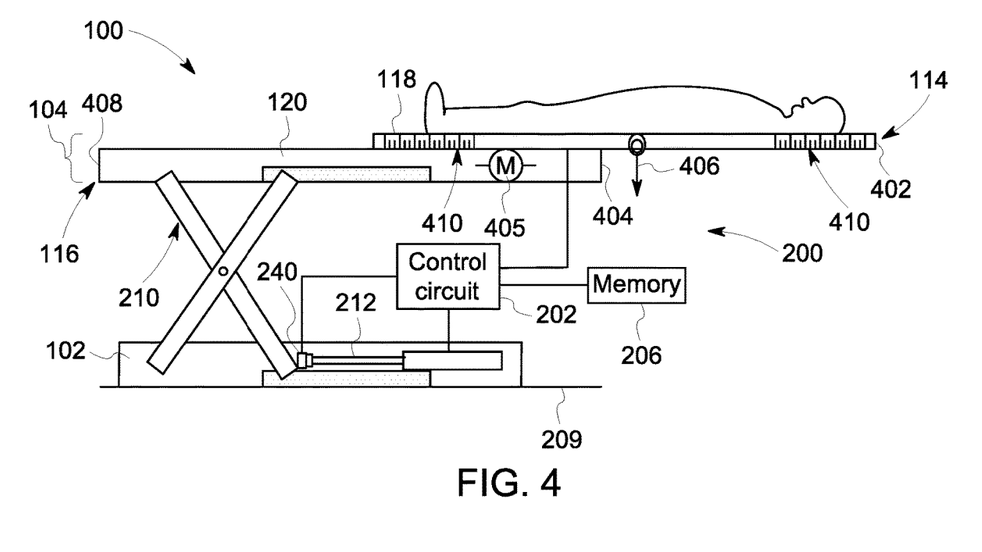
FIG. 4 illustrates the patient weight measuring system with a cradle of the patient table in an extended position according to an embodiment.

FIG. 4 illustrates the patient weight measuring system 200 with the cradle 118 of the patient table 100 in an extended position according to an embodiment. The cradle 118 is slidable relative to the platform 120. In the extended position, the cradle 118 is cantilevered such that a first end 402 of the cradle 118 projects beyond a corresponding first end 404 of the platform 120. The first end 402 of the cradle 118 projects farther beyond the first end 404 of the platform 120 in the extended position than in the retracted position of the cradle 118. For example, the cradle 118 is in the retracted position in FIG. 3, and the first end 402 of the cradle 118 approximately aligns with the first end 404 of the platform 120. Optionally, the first end 402 of the cradle 118 may project beyond the first end 404 of the platform 120 in both the retracted position and the extended position, but the first end 402 projects farther from the first end 404 in the extended position relative to the retracted position. The movement of the cradle 118 relative to the platform 120 may be automatically controlled by a table motor 405. Alternatively, the cradle 118 may be manually moved by an operator.

The tabletop 104 may include the extendable cradle 118 for loading and positioning the patient relative to medical imaging systems and/or devices. For example, the cradle 118 is extendable to load the patient into a gantry of a medical imaging device, such as an MRI imaging device, a CT imaging device, or the like, while the base 102, support frame 210, and at least a portion of the platform 120 remain outside of the gantry. In another example, the cradle 118 may extend to position the patient relative to a different imaging modality device, such as an ultrasound system or an X-ray system. The cradle 118 is extendable to control and select the region of the patient's body that is aligned with the medical imaging device.

In at least one embodiment, the patient weight measuring system 200 is configured to measure the patient's weight on the table 100 regardless of the positioning of the cradle 118 relative to the platform 120 and regardless of the positioning of the patient on the cradle 118. For example, the patient weight measuring system 200 can calculate the patient's weight while the cradle 118 is in the retracted position and/or while the cradle 118 is in the extended position as shown in FIG. 4. In FIG. 4, a center of mass or center of gravity 406 of the patient is located outside of a length of the platform 120 between the first end 404 of the platform 120 and a second end 408 of the platform 120 that defines the second end 116 of the tabletop 104. The center of mass 406 is located beyond the first end 404 of the platform 120. Even in the extended position of the cradle 118 with the patient's center of mass 406 outside of the length of the platform 120, the control circuit 202 is configured to calculate the weight of the patient based on the actuator force measured by the load sensor 240. The patient weight measurement system 200 is configured to accommodate changes in leverage and moment (e.g., torque) when calculating the weight of the patient on the tabletop 104.

Figure 5:
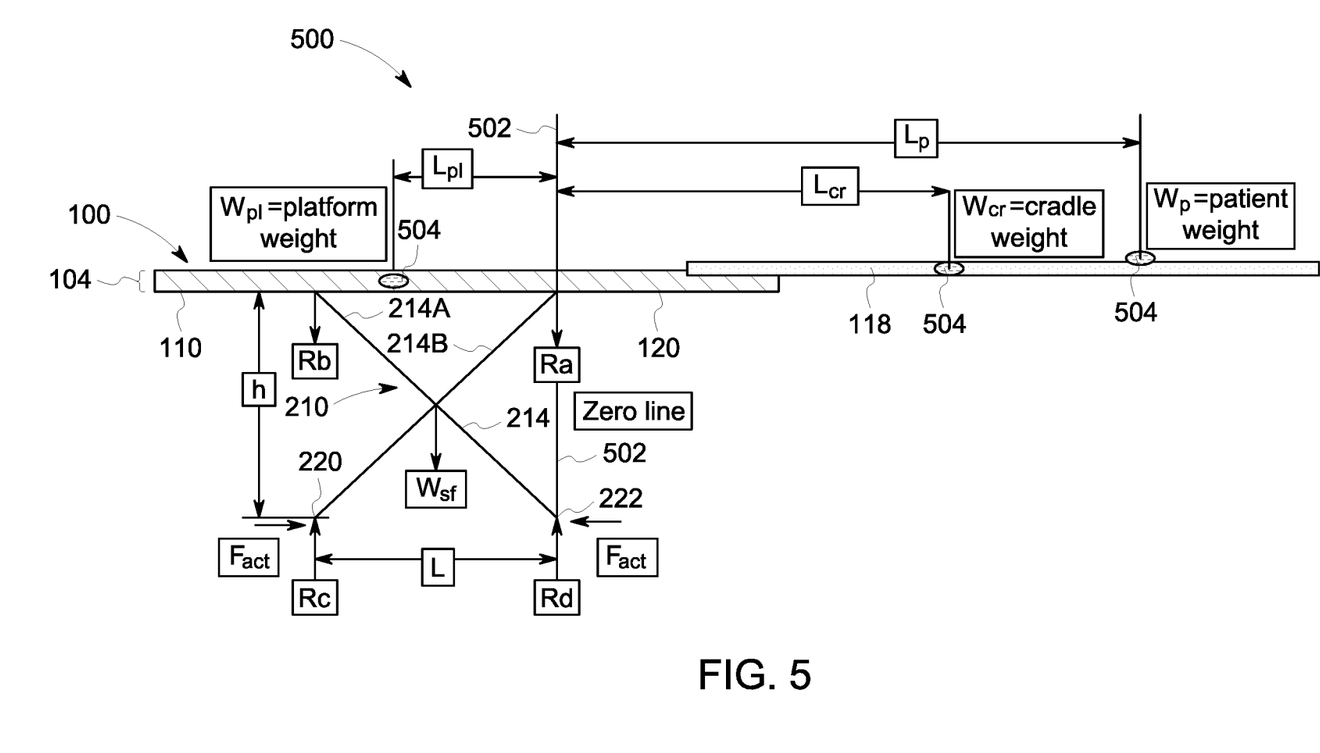
FIG. 5 is a force diagram showing various forces on the patient table when the cradle is in the extended position according to an embodiment.

According to one or more embodiments, the control circuit 202 of the patient weight measuring system 200 is configured to calculate the weight of the patient based on the actuator force measured by the load sensor 240 via a patient weight function. The patient weight function may be derived based on physics force diagrams and equations and/or calibrations using known weights. For example, FIG. 5 is a force diagram 500 showing various forces on the patient table 100 when the cradle 118 is in the extended position according to an embodiment. The force diagram 500 illustrates force directions and distances relative to a reference or zero line 502. The markers 504 labeled $W_{pl}$, $W_{cr}$, and $W_p$ represent the center of mass locations of the platform 120, the cradle 118, and the patient, respectively. The labels $L_{pl}$, $L_{cr}$, and $L_p$ represent the lengths or distances from the zero line 502 to the platform 120, cradle 118, and patient, respectively. The label $F_{act}$ represents the actuator force exerted by the actuator 212 (shown in FIG. 4) and measured by the load sensor 240 (FIG. 4). The label $W_{sf}$ represents the weight of the support frame 210. The label h generally represents the height of the tabletop 104 from a reference point, such as the floor 209 or the base 102 (both shown in FIG. 4). The height (h) may be the distance between the bottom side 110 of the tabletop 104 and the floor 209 (or between the bottom side 110 and the base 102). The label L represents the longitudinal length between ends of the two frame members 214, such as the length between the first end 220 of the frame member 214B and the second end 222 of the other frame member 214A. The labels $R_a$ and $R_b$ represent normal forces exerted on the support frame 210 at the two respective contact locations with the platform 120 of the tabletop 104. The labels $R_c$ and $R_d$ represent normal forces exerted on the support frame 210 at the two respective contact locations with the base 102 (or the floor 209).

The forces can be mathematically expressed as different torques or moments relative to the zero line 502. Combining and simplifying the expressions to solve for the patient weight ($W_p$) yields a patient weight function in which the patient weight varies based on the actuator force (Fact) and the height (h). The patient weight may also be affected by the length (L) and the weights of the platform ($W_{pl}$), the cradle ($W_{cr}$), and the support frame ($W_{sf}$). The weights of the platform, cradle, and support frame are constants, and may be known. The length (L) can be determined based on the height (h). For example, the length (L), height (h), and the frame members 214 define right triangles with the length of the frame members 214 representing the hypotenuse. Upon determining the height (h), the length (L) can be calculated using Pythagorean's theorem ($a^2+b^2=c^2$).

Figure 6:
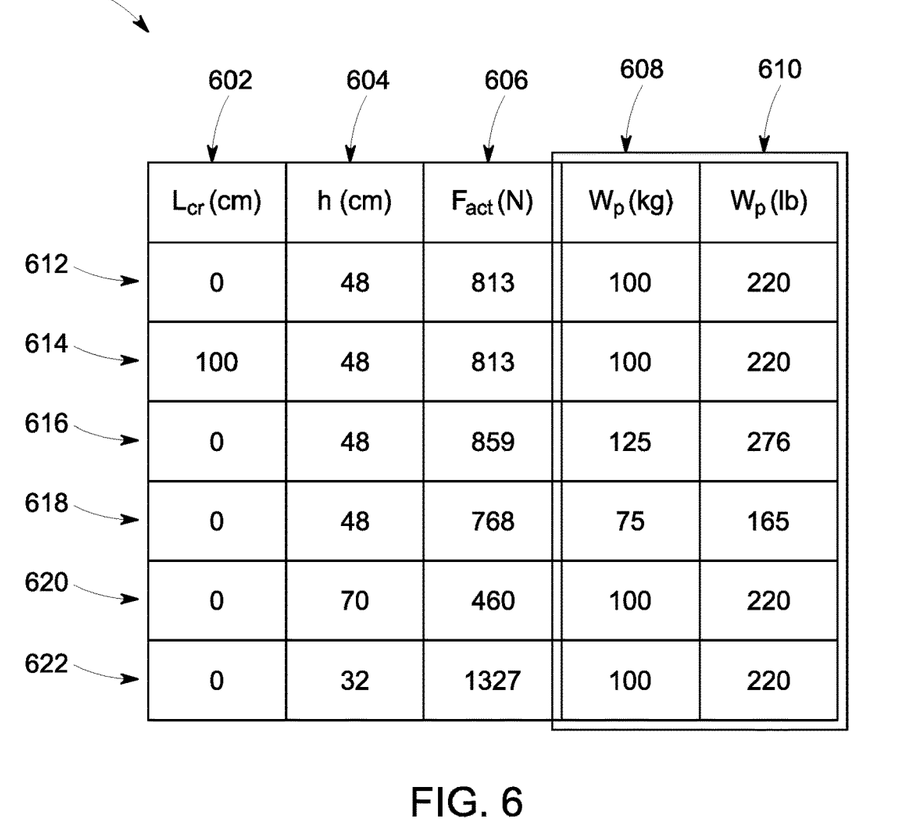
FIG. 6 is a table showing various patient weights calculated by the control circuit according to an embodiment.

FIG. 6 is a table 600 showing various patient weights calculated by the control circuit 202 according to an embodiment. For example, the control circuit 202 may calculate the patient weights by utilizing the derived patient weight function that is associated with the patient table 100 shown in FIGS. 1-5. The table 600 has a first column 602 that represents the length ($L_{cr}$) of the center of mass of the cradle 118 from the zero line 502 (shown in FIG. 5) measured in centimeters (cm); a second column 604 that represents the height (h) in cm; and a third column 606 that represents the actuator force ($F_{act}$) in Newtons (N). The values in the cells of the columns 602, 604, 606 may be inputs that are utilized by the control circuit 202 to calculate the patient weight. The table 600 also has a fourth column 608 that represents the patient weight (Wp) in kilograms (kg) and fifth column 610 that shows the same patient weight values in pounds (lb). The patient weight values in the cells of the fourth and fifth columns 608, 610 are the outputs that are generated by the control circuit 202 using the derived patient weight function based on the inputs and known information, such as known component weights and calibration constants.

In a first sample calculation shown in row 612, the cradle length (Lcr) is 0 such that the center of mass of the cradle 118 aligns with the zero line 502. The cradle 118 may be at or proximate to the retracted position when the cradle length is 0. The height (h) is determined to be 48 cm. In an embodiment, the height may be determined based on an actuator position signal received from the actuator 212 or a sensor that monitors an extension of the actuator 212. For example, the height of the support frame 210 is directly proportional to the extension of the bolt 232 from the housing 236 of the actuator 212. The height may be calibrated with the extension of the bolt 232 to be able to determine the height of the support frame 210 based on a measured position of the actuator 212. In another embodiment, the height can be calculated by measuring the angle between the first frame member 214A and the platform 120 (or the equivalent angle between the second frame member 214B and the base 102) and multiplying the sin of that angle by the individual lengths of the frame member 214. For example, the length of the frame member 214 is a hypotenuse in a right triangle, and multiplying the hypotenuse by the sin of the angle provides the length of the opposite side, which is the height (h). In yet another embodiment, the height can be measured using a proximity sensor, a range sensor, or the like.

Continuing with the other cells in the first row 612 associated with the first sample calculation, the actuator force ($F_{act}$) measured by the load sensor 240 is 813 N. The control circuit 202 inputs these values into the weight calculation function to calculate that the weight of the patient on the patient table 100 is 100 kg (220 lbs). Prior to performing a second sample calculation, the cradle 118 is moved to an extended position such that the center of mass of the cradle 118 is 100 cm (e.g., 1 m) from the zero line 502. The patient may be disposed on the cantilevered portion of the cradle 118 as shown in FIGS. 4 and 5. The results of the second sample calculation are shown in row 614. As shown, moving the cradle 118 to the extended position does not affect the measured actuator force, which still reads 813 N, and the calculate patient weight is also unchanged from the first sample calculation in row 612. Therefore, the patient weight function may be independent and unaffected by the positioning of the cradle 118 and the positioning of the patient relative to the tabletop 104.

For the third sample calculation shown in row 616, the height of the tabletop 104 and the positioning of the cradle 118 are the same as the first sample calculation, but a different, second patient is disposed on the cradle 118. The actuator force is measured to be 859 N, which is greater than the actuator force measured in the first sample calculation. Based on these inputs, the control circuit 202 calculates that the second patient weighs 125 kg (276 lb). The fourth sample calculation shown in row 618 is similar to the third sample calculation except that a different, third patient is on the patient table 100. The actuator force is measured to be 768 N, and the control circuit 202 calculates the third patient weight as 75 kg (165 lb).

A fifth sample calculation shown in row 620 is performed at a different height (h) of the tabletop 104 relative to the height (h) in the previous sample calculations. For example, the tabletop 104 is raised to a height (h) of 70 cm from the height of 48 cm. At 70 cm, the actuator force ($F_{act}$) measured by the load sensor 240 is 460 N, and the control circuit 202 calculates that the weight of the patient ($W_p$) is 100 kg (220 lb). For example, the same patient may be on the table 100 in both the first sample calculation in row 612 and the fifth sample calculation in row 620. The load sensor 240 measures a greater actuator force (813 N) at the lower height (h) in the first sample calculation than the actuator force (460 N) measured at the greater height (h). The tabletop 104 is lowered below 48 cm to 32 cm in a sixth sample calculation shown in row 622. At the lowered position, the actuator force ($F_{act}$) is measured to be 1327 N, and the control circuit 202 calculates the patient weight to be 100 kg (220 lb). The first, fifth, and sixth sample calculations indicate that the actuator force ($F_{act}$) is inversely related to the height (h) of the tabletop 104.

Referring back to FIG. 4, the patient weight measuring system 200 may be configured to utilize the calculated patient weight ($W_p$) to provide additional information. In the illustrated embodiment, the patient weight measuring system 200 may be configured to automatically calculate a body mass index (BMI) value for the patient. For example, the cradle 118 may have a built-in ruler with graduated markings 410 at regular intervals along at least portions of the length of the cradle 118, and optionally along the entire length of the cradle 118. The markings 410 are located along an outer edge 412 of the cradle 118 that faces towards a medical professional, such as a technician, nurse, doctor, or the like. The ruler enables the medical professional to determine the height of the patient that is on the cradle 118 by calculating the length between a marking 410 that aligns with the top of the patient's head and another marking 410 that aligns with the bottom of the patient's heel. In an embodiment, the ruler on the cradle 118 may be a digital ruler that is at least partially automated. For example, the medical professional may manually select the markings 410 aligning with the top of the head and the bottom of the heel using a user interface device, such as buttons along the outer edge 412, a slide device that slides along the outer edge 412, or the like. The control circuit 202 or another processing device receives the user inputs selecting the locations or markings 410 along the ruler associated with the ends of the patient, and may automatically calculate the difference in length between the two indicated markings 410 to determine the patient height.

The memory 206 may store BMI information, such as charts and/or look-up tables that correlate patient weight and height with BMI values. The control circuit 202 may access the BMI information from the memory 206 to determine the BMI value of the patient on the cradle 118 based on the calculated patient weight ($W_p$) and patient height. The patient information generated by the patient weight measuring system 200, such as patient weight, height, and BMI value, may be automatically recorded and stored in a private, secure digital file associated with the patient.

Figure 7:
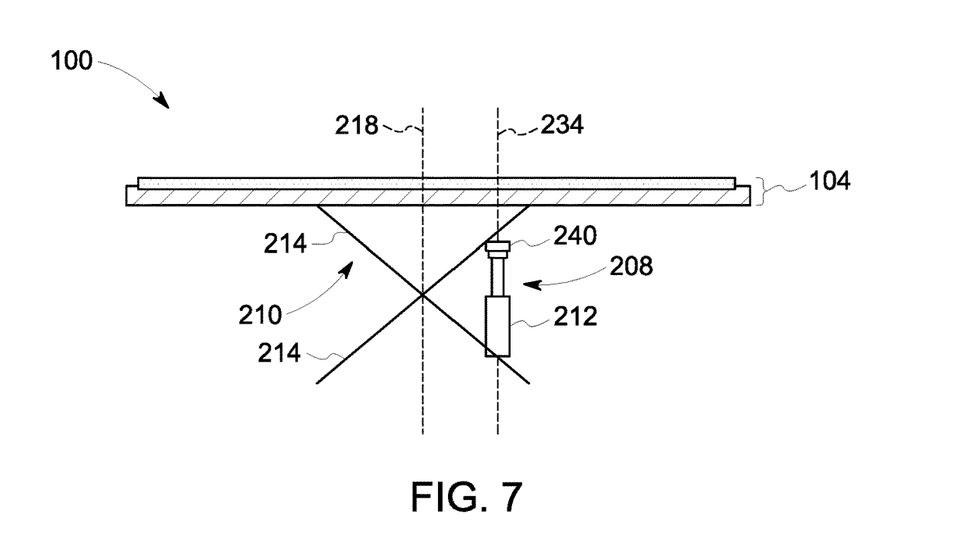
FIG. 7 illustrates the patient table with an elevation mechanism modified according to a first alternative embodiment.

FIG. 7 illustrates the patient table 100 with the elevation mechanism 208 modified according to a first alternative embodiment. In the illustrated embodiment, the support frame 210 is the same scissors linkage shown in FIGS. 2 through 5, but the actuator 212 is vertically oriented instead of horizontally oriented. For example, the actuator 212 is configured to move and to exert the actuator force in a direction along an actuator load axis 234 which is parallel to the vertical axis 218. In the illustrated embodiment, the actuator 212 is coupled to both of the frame members 214 and extends between the frame members 214. Alternatively, the actuator 212 may engage only one of the frame members 214. The load sensor 240 is disposed between the bolt 232 of the actuator 212 and the frame member 214, but the load sensor 240 may have another location along the actuator load axis 234 in another embodiment. A patient weight function may be derived that calculates the patient weight based on the actuation force measured by the load sensor 240. The patient weight function may be similar to the patient weight function derived for the embodiment shown in FIGS. 2 through 6. According to an embodiment, changes in the height (h) of the tabletop 104 may not affect the patient weight measurement for the table 100 having the illustrated elevation mechanism 208. For example, the patient weight may vary with the measured actuator force independently of tabletop height, patient location on the cradle, and cradle extension.

FIG. 8 illustrates the patient table 100 with the elevation mechanism 208 modified according to a second alternative embodiment. The support frame 210 has a parallelogram arrangement, such that the two frame members 214 are oriented parallel to each other. The actuator 212 engages one of the frame members 214 at an acute angle relative to the floor or the base. The actuator 212 exerts the actuation force along the actuator load axis 234, which is oblique to the vertical axis 218 (e.g., not parallel or perpendicular). A patient weight function may be derived to calculate the patient weight based on the actuation force measured by the load sensor 240 for the elevation mechanism 208 shown in FIG. 8, similar to the patient weight function described with reference to the embodiment shown in FIGS. 2 through 6.

Figure 9:
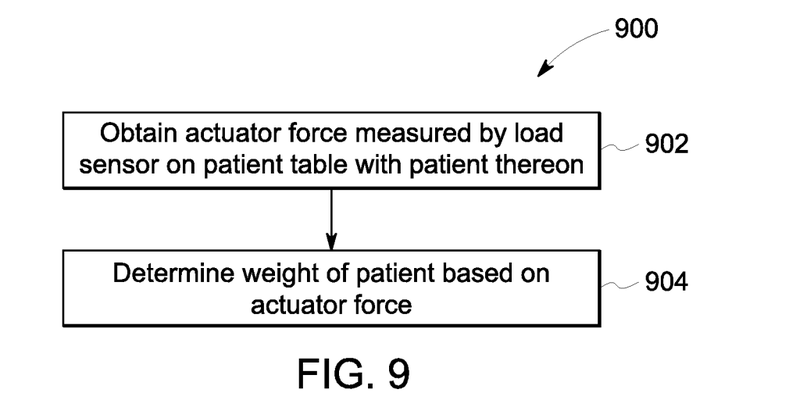
FIG. 9 is a flowchart of a method for measuring a patient weight according to an embodiment.

FIG. 9 is a flowchart of a method 900 for measuring a patient weight according to an embodiment. The method 900 may represent at least some of the operations performed by the control circuit 202, including the one or more processors 204 thereof, of the patient weight measuring system 200 shown in FIG. 2. The method 900 may represent an algorithm used to create (e.g., write) one or more software applications that direct operation of one or more processors 204 of the control circuit 202. The method 900 may include additional steps, fewer steps, and/or different steps than the illustrated flowchart in FIG. 9 in an alternative embodiment.

Referring to FIGS. 1 through 8, the method 900 begins at 902, at which an actuator force measured by a load sensor 240 on a patient table 100 is obtained. The patient table 100 includes a tabletop 104 configured to receive a patient thereon. The patient table 100 includes an elevation mechanism 208 that has a support frame 210 and an actuator 212. The support frame 210 has multiple pivotable frame members 214 mechanically connected to the tabletop 104. The actuator 212 is configured to exert the actuator force on at least one of the frame members 214 to control a height of the tabletop 104 relative to a floor 209. The load sensor 240 is disposed along an actuator load axis 234 of the actuator 212, and the load sensor 240 measures the actuator force while the patient is on the tabletop 104.

At 904, a weight of the patient that is disposed on the patient table 100 is determined based on the actuator force measured by the load sensor 240. For example, the actuator force measurement (e.g., $F_{act}$) may be input into a derived patient weight function, and the patient weight may be calculated as the output of the patient weight function. The patient weight function may be based on physics-based formulas and equations and/or calibrations.

In one or more embodiments, a patient table is provided that includes a tabletop, an elevation mechanism, a load sensor, and a control circuit. The tabletop is configured to receive a patient thereon. The elevation mechanism is configured to adjust a height of the tabletop relative to a floor. The elevation mechanism includes a support frame and an actuator. The support frame includes multiple pivotable frame members mechanically connected to the tabletop. The actuator is configured to exert an actuator force on at least one of the frame members to control the height of the tabletop. The load sensor is operably connected to the actuator and configured to measure the actuator force. The control circuit is communicatively connected to the load sensor, and is configured to calculate a weight of the patient disposed on the tabletop based on the actuator force measured by the load sensor.

Optionally, the tabletop includes a platform and a cradle. The cradle is slidably coupled to the platform and configured to move relative to the platform between a retracted position and an extended position. The cradle receives the patient thereon, and a first end of the cradle projects farther beyond a first end of the platform in the extended position than in the retracted position to load the patient into a gantry of an imaging system. Optionally, the control circuit is configured to calculate the weight of the patient disposed on the cradle based on the actuator force measured by the load sensor during a time that the cradle is in the extended position relative to the platform of the tabletop.

Optionally, the support frame includes a scissor linkage and two of the frame members intersect one another at a point of intersection and are pivotably connected to one another via a link at the point of intersection.

Optionally, the actuator exerts the actuator force on the at least one of the frame members in a direction along an actuator load axis, and the load sensor is configured to measure the actuator force along the actuator load axis.

Optionally, the elevation mechanism is configured to adjust the height of the tabletop by moving the tabletop along a vertical axis. The actuator is oriented to exert the actuator force on the at least one of the frame members in a direction perpendicular to the vertical axis.

Optionally, the elevation mechanism is configured to adjust the height of the tabletop by moving the tabletop along a vertical axis. The actuator is oriented to exert the actuator force on the at least one of the frame members in a direction parallel to the vertical axis.

Optionally, the control circuit is operably connected to the actuator and is configured to receive an actuator position signal from the actuator that indicates a current position of the actuator. The control circuit is configured to determine the height of the tabletop based on the actuator position signal and to calculate the weight of the patient disposed on the tabletop based on both the actuator force and the height of the tabletop.

Optionally, the actuator force measured by the load sensor is the only force measurement utilized by the control circuit to calculate the weight of the patient disposed on the tabletop.

Optionally, the tabletop includes a digital ruler longitudinally extending along an outer edge of the tabletop. The control circuit is configured to receive user inputs selecting two locations along the digital ruler associated with corresponding ends of the patient, and to calculate a body mass index of the patient based on the weight of the patient that is calculated and a height of the patient that is equivalent to a length between the two locations along the digital ruler.

In one or more embodiments, a patient weight measuring system is provided that includes a patient table and a control circuit. The patient table includes a tabletop, a support frame, an actuator, and a load sensor. The tabletop is configured to receive a patient thereon. The support frame includes multiple pivotable frame members mechanically connected to the tabletop. Two of the frame members intersect one another at a point of intersection and are pivotably connected to one another via a link at the point of intersection to define a scissor linkage. The actuator is configured to modify an actuator force exerted by the actuator on at least one of the two frame members of the scissor linkage to adjust a height of the tabletop relative to a floor. The load sensor engages the actuator and is configured to measure the actuator force. The control circuit is communicatively connected to the load sensor of the patient table. The control circuit is configured to calculate a weight of the patient disposed on the tabletop based on the actuator force measured by the load sensor.

Optionally, the tabletop includes a platform and a cradle. The cradle is slidably coupled to the platform and is configured to move relative to the platform between a retracted position and an extended position. The cradle receives the patient thereon, and a first end of the cradle projects farther beyond a first end of the platform in the extended position than in the retracted position to load the patient into a gantry of an imaging system. Optionally, the control circuit is configured to calculate the weight of the patient disposed on the cradle based on the actuator force measured by the load sensor during a time that the cradle is in the extended position relative to the platform of the tabletop.

Optionally, the actuator exerts the actuator force on the at least one of the frame members in a direction along an actuator load axis, and the load sensor is configured to measure the actuator force along the actuator load axis.

Optionally, the control circuit is operably connected to the actuator and is configured to receive an actuator position signal from the actuator that indicates a current position of the actuator. The control circuit is configured to determine the height of the tabletop based on the actuator position signal and to calculate the weight of the patient disposed on the tabletop based on both the actuator force and the height of the tabletop.

Optionally, the actuator force measured by the load sensor is the only force measurement utilized by the control circuit to calculate the weight of the patient disposed on the tabletop.

Optionally, the tabletop includes a digital ruler longitudinally extending along an outer edge of the tabletop. The control circuit is configured to receive user inputs selecting two locations along the digital ruler associated with corresponding ends of the patient, and to calculate a body mass index of the patient based on the weight of the patient that is calculated and a height of the patient that is equivalent to a length between the two locations along the digital ruler.

Optionally, the tabletop longitudinally extends from a first end of the tabletop to a second end of the tabletop. The control circuit is configured to calculate the weight of the patient disposed on the tabletop at any location of the center of mass of the patient between the first end and the second end.

In one or more embodiments, a patient table is provided that includes a tabletop, an elevation mechanism, a load sensor, and a control circuit. The tabletop includes a platform and a cradle that is slidably coupled to the platform. The cradle is controllable to move relative to the platform between a retracted position and an extended position. The cradle receives a patient thereon, and a first end of the cradle projects beyond a first end of the platform in the extended position to load the patient into a gantry of an imaging system. The elevation mechanism is configured to adjust a height of the tabletop relative to a floor. The elevation mechanism includes a support frame and an actuator. The support frame includes multiple pivotable frame members mechanically connected to the tabletop. The actuator is configured to exert an actuator force on at least one of the frame members in a direction along an actuator load axis to control the height of the tabletop. The load sensor is operably connected to the actuator and configured to measure the actuator force along the actuator load axis. The control circuit is communicatively connected to the load sensor. The control circuit is configured to calculate a weight of the patient disposed on the cradle based on the actuator force measured by the load sensor while the cradle is at either of the retracted position or the extended position.

Optionally, the control circuit is operably connected to the actuator and is configured to receive an actuator position signal from the actuator that indicates a current position of the actuator. The control circuit is configured to determine the height of the tabletop based on the actuator position signal and to calculate the weight of the patient disposed on the tabletop based on both the actuator force and the height of the tabletop.

In one or more embodiments, a method (e.g., for measuring a patient weight) is provided. The method includes obtaining an actuator force measured by a load sensor on a patient table. The patient table includes a tabletop configured to receive a patient thereon, and also includes an elevation mechanism that has a support frame and an actuator. The support frame has multiple pivotable frame members mechanically connected to the tabletop. The actuator is configured to exert the actuator force on at least one of the frame members to control a height of the tabletop relative to a floor. The load sensor is disposed along an actuator load axis of the actuator, and the actuator force is measured by the load sensor while the patient is on the tabletop. The method also includes determining, via one or more processors, a weight of the patient that is disposed on the patient table based on the actuator force measured by the load sensor.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are example embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient table comprising:
a tabletop configured to receive a patient thereon;
an elevation mechanism configured to adjust a height of the tabletop relative to a floor, the elevation mechanism including a support frame and an actuator, the support frame including multiple pivotable frame members mechanically connected to the tabletop, the actuator configured to exert an actuator force on at least one of the frame members to control the height of the tabletop;
a load sensor operably connected to the actuator and configured to measure the actuator force; and
a control circuit communicatively connected to the load sensor, the control circuit configured to calculate a weight of the patient disposed on the tabletop based on the actuator force measured by the load sensor.

2. The patient table of claim 1, wherein the tabletop includes a platform and a cradle, the cradle slidably coupled to the platform and configured to move relative to the platform between a retracted position and an extended position, wherein the cradle receives the patient thereon and a first end of the cradle projects farther beyond a first end of the platform in the extended position than in the retracted position to load the patient into a gantry of an imaging system.

3. The patient table of claim 2, wherein the control circuit is configured to calculate the weight of the patient disposed on the cradle based on the actuator force measured by the load sensor during a time that the cradle is in the extended position relative to the platform of the tabletop.

4. The patient table of claim 1, wherein the support frame includes a scissor linkage and two of the frame members intersect one another at a point of intersection and are pivotably connected to one another via a link at the point of intersection.

5. The patient table of claim 1, wherein the actuator exerts the actuator force on the at least one of the frame members in a direction along an actuator load axis, and the load sensor is configured to measure the actuator force along the actuator load axis.

6. The patient table of claim 1, wherein the elevation mechanism is configured to adjust the height of the tabletop by moving the tabletop along a vertical axis, and wherein the actuator is oriented to exert the actuator force on the at least one of the frame members in a direction perpendicular to the vertical axis.

7. The patient table of claim 1, wherein the elevation mechanism is configured to adjust the height of the tabletop by moving the tabletop along a vertical axis, and wherein the actuator is oriented to exert the actuator force on the at least one of the frame members in a direction parallel to the vertical axis.

8. The patient table of claim 1, wherein the control circuit is operably connected to the actuator and is configured to receive an actuator position signal from the actuator that indicates a current position of the actuator, wherein the control circuit is configured to determine the height of the tabletop based on the actuator position signal and to calculate the weight of the patient disposed on the tabletop based on both the actuator force and the height of the tabletop.

9. The patient table of claim 1, wherein the actuator force measured by the load sensor is the only force measurement utilized by the control circuit to calculate the weight of the patient disposed on the tabletop.

10. The patient table of claim 1, wherein the tabletop includes a digital ruler longitudinally extending along an outer edge of the tabletop, wherein the control circuit is configured to receive user inputs selecting two locations along the digital ruler associated with corresponding ends of the patient, and to calculate a body mass index of the patient based on the weight of the patient that is calculated and a height of the patient that is equivalent to a length between the two locations along the digital ruler.

11. A patient weight measuring system comprising:
a patient table comprising a tabletop, a support frame, an actuator, and a load sensor, the tabletop configured to receive a patient thereon, the support frame including multiple pivotable frame members mechanically connected to the tabletop, two of the frame members intersecting one another at a point of intersection and being pivotably connected to one another via a link at the point of intersection to define a scissor linkage, the actuator configured to modify an actuator force exerted by the actuator on at least one of the two frame members of the scissor linkage to adjust a height of the tabletop relative to a floor, the load sensor engaging the actuator and configured to measure the actuator force; and
a control circuit communicatively connected to the load sensor of the patient table, the control circuit configured to calculate a weight of the patient disposed on the tabletop based on the actuator force measured by the load sensor.

12. The patient weight measuring system of claim 11, wherein the tabletop includes a platform and a cradle, the cradle slidably coupled to the platform and configured to move relative to the platform between a retracted position and an extended position, wherein the cradle receives the patient thereon and a first end of the cradle projects farther beyond a first end of the platform in the extended position than in the retracted position to load the patient into a gantry of an imaging system.

13. The patient weight measuring system of claim 12, wherein the control circuit is configured to calculate the weight of the patient disposed on the cradle based on the actuator force measured by the load sensor during a time that the cradle is in the extended position relative to the platform of the tabletop.

14. The patient weight measuring system of claim 11, wherein the actuator exerts the actuator force on the at least one of the frame members in a direction along an actuator load axis, and the load sensor is configured to measure the actuator force along the actuator load axis.

15. The patient weight measuring system of claim 11, wherein the control circuit is operably connected to the actuator and is configured to receive an actuator position signal from the actuator that indicates a current position of the actuator, wherein the control circuit is configured to determine the height of the tabletop based on the actuator position signal and to calculate the weight of the patient disposed on the tabletop based on both the actuator force and the height of the tabletop.

16. The patient weight measuring system of claim 11, wherein the actuator force measured by the load sensor is the only force measurement utilized by the control circuit to calculate the weight of the patient disposed on the tabletop.

17. The patient weight measuring system of claim 11, wherein the tabletop includes a digital ruler longitudinally extending along an outer edge of the tabletop, wherein the control circuit is configured to receive user inputs selecting two locations along the digital ruler associated with corresponding ends of the patient, and to calculate a body mass index of the patient based on the weight of the patient that is calculated and a height of the patient that is equivalent to a length between the two locations along the digital ruler.

18. The patient weight measuring system of claim 11, wherein the tabletop longitudinally extends from a first end of the tabletop to a second end of the tabletop, and wherein the control circuit is configured to calculate the weight of the patient disposed on the tabletop at any location of the center of mass of the patient between the first end and the second end.

19. A patient table comprising:
   a tabletop including a platform and a cradle that is slidably coupled to the platform, the cradle controllable to move relative to the platform between a retracted position and an extended position, wherein the cradle receives a patient thereon and a first end of the cradle projects beyond a first end of the platform in the extended position to load the patient into a gantry of an imaging system;
   an elevation mechanism configured to adjust a height of the tabletop relative to a floor, the elevation mechanism including a support frame and an actuator, the support frame including multiple pivotable frame members mechanically connected to the tabletop, the actuator configured to exert an actuator force on at least one of the frame members in a direction along an actuator load axis to control the height of the tabletop;
   a load sensor operably connected to the actuator and configured to measure the actuator force along the actuator load axis; and
   a control circuit communicatively connected to the load sensor, the control circuit configured to calculate a weight of the patient disposed on the cradle based on the actuator force measured by the load sensor while the cradle is at either of the retracted position or the extended position.

20. The patient table of claim 19, wherein the control circuit is operably connected to the actuator and is configured to receive an actuator position signal from the actuator that indicates a current position of the actuator, wherein the control circuit is configured to determine the height of the tabletop based on the actuator position signal and to calculate the weight of the patient disposed on the tabletop based on both the actuator force and the height of the tabletop.

21. A method comprising:
   obtaining an actuator force measured by a load sensor on a patient table that includes a tabletop configured to receive a patient thereon, the patient table including an elevation mechanism that has a support frame and an actuator, the support frame having multiple pivotable frame members mechanically connected to the tabletop, the actuator configured to exert the actuator force on at least one of the frame members to control a height of the tabletop relative to a floor, wherein the load sensor is disposed along an actuator load axis of the actuator and the actuator force is measured by the load sensor while the patient is on the tabletop; and
   determining, via one or more processors, a weight of the patient that is disposed on the patient table based on the actuator force measured by the load sensor.

* * * * *